United States Patent [19]

James

[11] Patent Number: 4,632,117
[45] Date of Patent: Dec. 30, 1986

[54] SIMPLIFIED TRANSCUTANEOUS NERVE STIMULATING DEVICE

[75] Inventor: Donald N. James, Estes Park, Colo.

[73] Assignee: Staodynamics, Inc., Longmont, Colo.

[21] Appl. No.: 762,522

[22] Filed: Aug. 5, 1985

Related U.S. Application Data

[63] Continuation of Ser. No. 406,606, Aug. 9, 1982, abandoned.

[51] Int. Cl.⁴ ............................................. A61N 1/32
[52] U.S. Cl. ..................................................... 128/421
[58] Field of Search ........ 128/419 P, 419 T, 421–423, 128/903–904, 908

[56] References Cited

U.S. PATENT DOCUMENTS

| | | | |
|---|---|---|---|
| 3,077,884 | 2/1963 | Batrow et al. | 128/423 R |
| 3,521,087 | 7/1970 | Lombardi | 128/908 |
| 3,656,025 | 4/1972 | Roveti | 128/908 |
| 3,808,502 | 4/1974 | Babilius | 128/908 |
| 3,835,865 | 9/1974 | Bowers | 128/421 |
| 4,121,594 | 10/1978 | Miller et al. | 128/422 |
| 4,147,171 | 4/1979 | Greene et al. | 128/421 |
| 4,155,366 | 5/1979 | DiMucci | 128/421 |
| 4,159,018 | 6/1979 | Brastad | 128/904 |
| 4,230,121 | 10/1980 | Stanton | 128/422 |
| 4,342,317 | 8/1982 | Axelgaard | 128/421 |

Primary Examiner—William E. Kamm
Assistant Examiner—Mitchell J. Shein
Attorney, Agent, or Firm—Robert E. Harris

[57] ABSTRACT

A simplified transcutaneous nerve stimulating device is disclosed that combines simplicity of structure with dependability of operation. The device utilizes a 45 volt battery source for circuitry simplification by eliminating the need for circuitry such as voltage multipliers, with the battery source powering an oscillator and a pair of constant current regulated drive circuits from which pulses are alternately coupled to isolated output pairs connectable with electrodes positionable on the skin of a user for imparting stimulation pulses to the body of the user for pain suppression.

4 Claims, 3 Drawing Figures

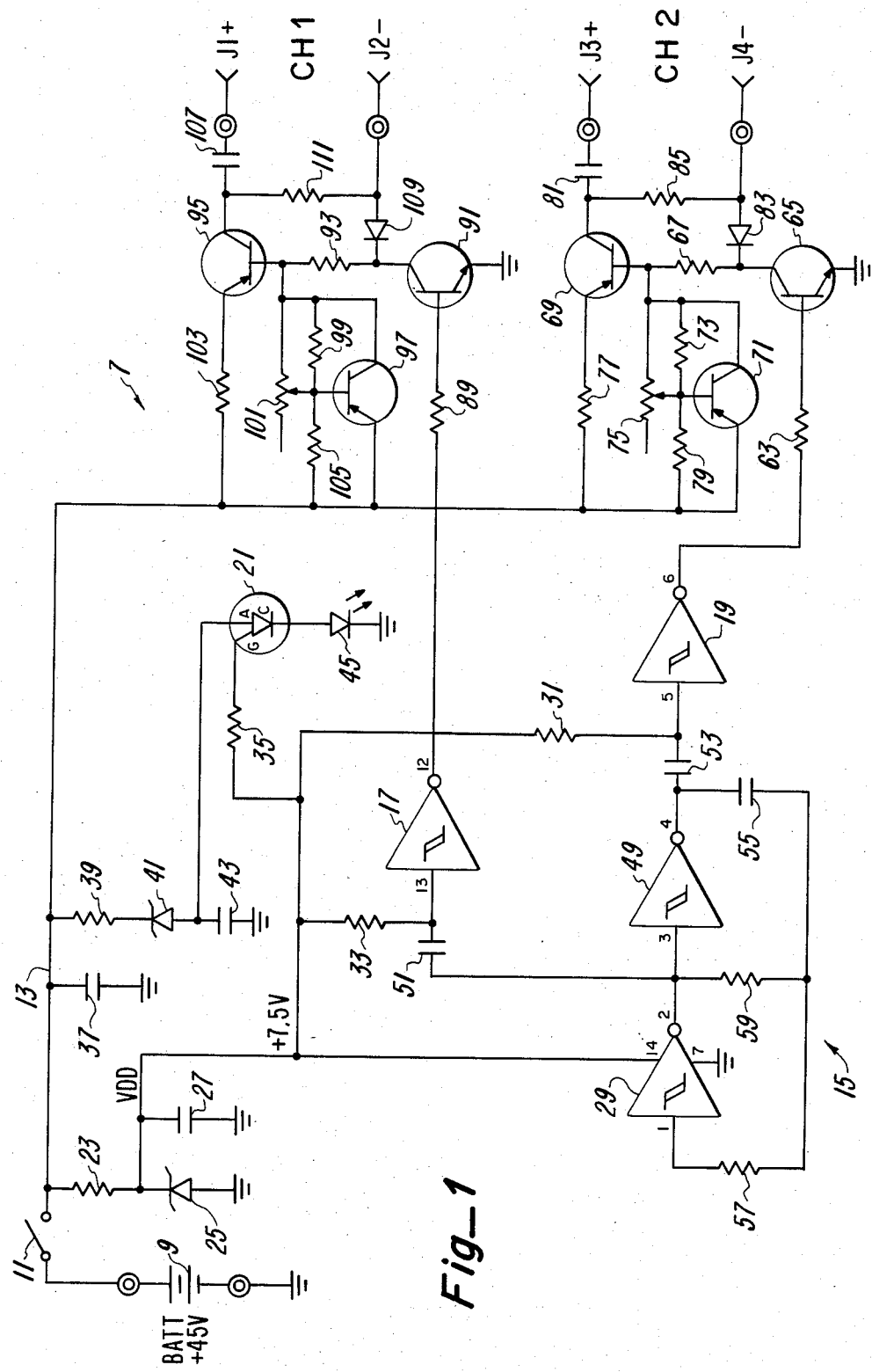
Fig_1

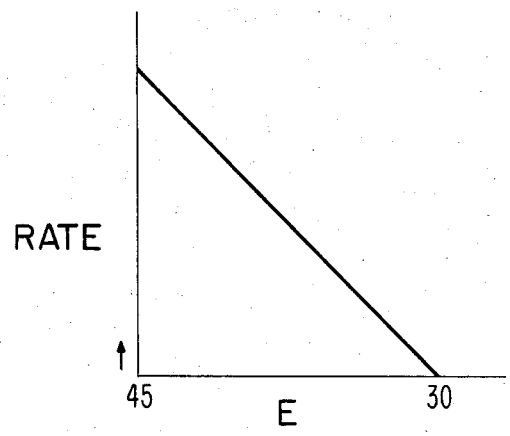
Fig_2
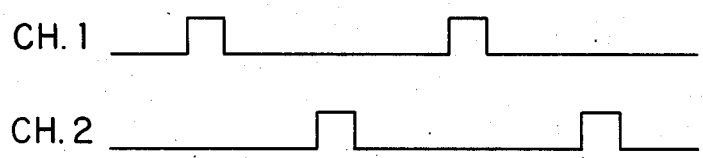
Fig_3

SIMPLIFIED TRANSCUTANEOUS NERVE STIMULATING DEVICE

This application is a continuation of U.S. patent application Ser. No. 406,606, filed Aug. 9, 1982, and entitled "Simplified Transcutaneous Nerve Stimulating Device", now abandoned.

FIELD OF THE INVENTION

This invention relates to transcutaneous nerve stimulating devices and, more particularly, relates to a transcutaneous nerve stimulating device of simplified structure.

BACKGROUND OF THE INVENTION

Transcutaneous nerve stimulating devices are well known and various devices have been heretofore suggested and/or utilized for pain suppression. One group of such devices commonly generates pulses (the frequency, magnitude and width of which vary from device to device and/or are adjustable in frequency, magnitude and/or width) which are coupled through driving circuitry to non-invasive electrodes in contact with the skin of a user.

Examples of transcutaneous nerve stimulators can be found in U.S. Pat. No. 4,014,347, 4,121,594, 4,147,171, and 4,084,595.

While at least some transcutaneous nerve stimulating structures now known have been found to be acceptable for some uses, such devices have not been found to be complete acceptable due, at least in part, to the necessity for relatively complicated (and hence high cost) circuitry or components thereof, failure to provide dependable operation with minimal battery drain, and/or failure to provide adequate circuitry enabling delivery of isolated pulse signals from a plurality of outputs.

SUMMARY OF THE INVENTION

This invention provides an improved transcutaneous nerve stimulating device that is of simple structure yet is dependable in operation.

It is an object of this invention to provide an improved transcutaneous nerve stimulating device.

It is another object of this invention to provide an improved transcutaneous nerve stimulating device that is of simple structure yet is dependable in operation.

It is another object of this invention to provide an improved transcutaneous nerve stimulating device that is disposable.

It is still another object of this invention to provide an improved transcutaneous nerve stimulating device that eliminates the need for complicated circuitry such as voltage multipliers.

It is another object of this invention to provide an improved transcutaneous nerve stimulating device that provides isolated outputs from a plurality of electrode pairs.

It is still another object of this invention to provide an improved transcutaneous nerve stimulating device that provides a constant current regulated output.

With these and other objects in view, which will become apparent to one skilled in the art as the description proceeds, this invention resides in the novel construction, combination, and arrangement of parts substantially as hereinafter described, and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which;

FIG. 1 is a schematic diagram of the transcutaneous nerve stimulating device of this invention;

FIG. 2 is a graph of battery voltage vs. rate of light emitting diode (LED) energization and de-energization for the LED shown in FIG. 1; and FIG. 3 is a typical waveform output for the dual channel outputs of the device illustrating the timewise spacing between pulses from channel to channel.

DESCRIPTION OF THE INVENTION

Transcutaneous nerve stimulating device 7 is shown in FIG. 1 to utilize a +45 volt battery 9 as the sole power source for the device. Through the use of such a battery source, the remaining circuitry of the device is simplified by eliminating the need for voltage multipliers (such as transformers and the like).

With such simplification, battery drainage during use is minimized to thus provide longer device life with a given battery power supply. Due to circuit simplification and the relatively long life gained through such simplification, the transcutaneous nerve stimulator of this invention has been adapted for a single use (i.e., is disposable) and may be discarded after battery depletion. To this end, switch 11 may be a one time switch, which once closed to power the unit remains closed so that the device is thereafter constantly powered. This can be achieved, for example, by use of an insulating tab positioned between switch contacts (which are biased toward contact with one another) with the tab having a portion external to the device case (not shown) so that the tab, when pulled or removed, allows the switch contacts to thereafter engage one another.

As shown in FIG. 1, switch 11 has one contact connected with battery power supply 9 and the other contact connected with lead 13 which supplies the positive DC voltage to power the device.

Power is supplied to square wave oscillator 15 (operating at a frequency of about 70 HZ), one shot buffer drivers 17 and 19, and the gate input of programmable unijunction transistor 21 through resistor 23, which resistor has one side connected to one side of Zener diode 25 and capacitor 27 (the other side of diode 25 and capacitor 27 being connected with ground). As indicated, the junction of resistor 23 and Zener diode 25 (7.5 volts) is directly connected with pin 14 of integrated circuit 29 (of oscillator 15), is connected with the input of one shot buffer drivers 17 and 19 through resistors 31 and 33, respectively, and is connected with the gate input of transistor 21 through resistor 35.

Lead 13 (which has a capacitor 37 to ground connected thereto) also supplies the positive DC voltage through resistor 39 to one side of 22 volt Zener diode 41, the other side of which diode is connected through capacitor 43 to ground and to one input of transistor 21. The other input of transistor 21 is connected with LED 45.

Programmable unijunction transistor 21 and energy storage capacitor 43 (having a charging path through resistor 39 and diode 41) form a low frequency oscillator for causing LED 45 to alternately be energized and de-energized to indicate that the device is powered. When capacitor 43 charges to the gate voltage of transistor 21, the unijunction transistor fires and causes a current surge to flow through LED 45 which causes the LED to "blink".

Battery source 9 supplies a +45 volt power supply to lead 13 only when the battery is fully charged, with the voltage supplied by the battery source decreasing as the battery discharges. To indicate that the battery is discharging, the rate of energization and de-energization (i.e. the "blinking" rate) of LED 45 is decreased basically in proportion to the decrease in voltage supplied by the battery (as shown typically in FIG. 2). When the useful life of the battery is assumed to end (i.e. when the battery is able to supply only about a 30 volt output), the LED will cease to be alternately energized and de-energized and the absence of the "blinking" light indication signals that the device is to be discarded.

Square wave oscillator 15 includes integrated circuits 29 and 49 with the output of integrated circuit 29 being connected with the input of integrated circuit 49 and with the input of one shot buffer driver 17 through capacitor 51. The output of integrated circuit 49 is connected through capacitor 53 to the input of one shot buffer driver 19, is connected through capacitor 55 and resistor 57 to the input of integrated circuit 29, and is connected through capacitor 55 and resistor 59 to the output of integrated circuit 29.

The output from one shot buffer driver 19 supplies the channel two oscillator output which is coupled through resistor 63 to transistor 65 (which is the control transistor for channel two). The collector of transistor 65 is connected through resistor 67 to the base of transistor 69 which provides a controlled output current. The junction of resistor 67 and the base of transistor 69 is connected to the collector of regulator transistor 71, is connected through resistor 73 to the base of transistor 71, and is connected to one side of variable resistor 75 (the movable wiper of which is connected with the base of transistor 71). Lead 13 (the DC power supply lead) is connected with the emitter of transistor 69 through resistor 77, is directly connected with the emitter of transistor 71, and is connected with the base of transistor 71 through resistor 79.

The positive output terminal (jack J3) for channel two is connected with the collector of transistor 69 through capacitor 81, while the negative output terminal (jack J4) is connected with the collector of transistor 65 through diode 83, with the collector of transistor 69 being connected through resistor 85 to the negative output.

The output from one shot buffer driver 17 supplies the channel one oscillator output which is connected through resistor 89 to the base of transistor 91 (which is the control transistor for channel one). The collector of transistor 91 is connected through resistor 93 to the base of transistor 95 which provides a controlled output current. The junction of resistor 93 and the base of transistor 95 is connected to the collector of regulator transistor 97, is connected through resistor 99 to the base of transistor 97, and is connected to one side of variable resistor 101 (the movable wiper of which is connected with the base of transistor 97). Lead 13 (the DC power supply lead) is connected with the emitter of transistor 95 through resistor 103, is directly connected with the emitter of transistor 97, and is connected with the base of transistor 97 through resistor 105.

The positive output terminal (jack J1) for channel one is connected with the collector of transistor 95 to capacitor 107, while the negative output terminal (jack J2) is connected with the collector transistor 91 through diode 109, with the collector of transistor 95 being connected through resistor 111 to the negative output.

The output pulses from the dual channels are timewise spaced and isolated from one another, as indicated in FIG. 3. Channel to channel output isolation is achieved and maintained by transistors 65 and 69 in channel two and transistors 91 and 95 in channel one.

In operation, when the output from integrated circuit 29 is negative going, this causes the output of integrated circuit 17 to go high (for a period of about 125 microseconds). When the output of integrated circuit 17 goes high, transistor 91 is turned on which activates transistors 95 and 97 to supply a constant output current, the magnitude of which is controlled by variable resistor 101. The constant output current is coupled through resistor 103, transistor 95, capacitor 107 and jack J1 to a load (connectable with jacks J1 and J2). The current is returned through jack J2, diode 109 and ground through resistor 95 (while transistor 91 is turned on).

In like manner, when the output from integrated circuit 49 is negative going, this causes the output of integrated circuit 19 to go high (for a period of about 125 micro-seconds). When the output of integrated circuit 19 goes high, transistor 65 is turned on which activates transistors 69 and 71 to supply a constant output current the magnitude of which is controlled by variable resistor 75. The constant output current is coupled through resistor 77, transistor 69, capacitor 81 and jack J3 to a load (connectable with jacks J3 and J4). The current is returned through jack J4, diode 83 and ground through transistor 65 (while transistor 65 is turned on).

The output appearing at jack J3 is 180° out of phase with respect to the output appearing at jack J1. This provides extremely high isolation between the two output channels.

The following components have been found to be usable in a working embodiment of this invention:

Resistors: 23-300K; 31-130K; 33-130K; 35-10K; 39-1.8M; 57-1.8M; 59-1.2M; 63-5.1K; 6727K; 73-11K; 75-0 to 50K; 77-10; 79-6.2K; 85-10K; 89-5.1K; 93-27K; 99-11K; 101-0 to 50K; 103-10; 105-6.2K; and 111-10K.

Capacitors: 27-6.8MF; 37-4.7MF; 43-1MF; 51-0.001MF; 53-0.001MF; 55-0.0047MF; 81-10MF; and 107-10MF.

Integrated circuits: 17, 19, 29 and 49-HEF-40106BT

Zener Diodes: 25-MMBZ5236; and 41-MMBZ5251.

LED: 45-MV54.

Diodes: 83-MMBD6050; and 109-MMBD6050.

Transistors: 65-MMBTA06; 69-MMBTA56; 71-MMBTA56; 91-MMBTA06; 95-MMBTA56; and 97-MMBTA56.

Programmable Unijunction Transistor: 21-MMBT6028.

The foregoing list is, however, meant only to be illustrative of a working embodiment, and the invention is not meant to be limited to the precise components and/or values listed.

As can be appreciated from the foregoing, this invention provides a transcutaneous nerve stimulating device that is of simple construction enabling effective use of the device as a disposable unit.

What is claimed is:

1. A transcutaneous nerve stimulating device, comprising:
   battery means;
   oscillating means connected with said battery means, said oscillating means including first and second signal providing means with said first signal providing means providing first output pulses and said second signal providing means providing second output pulses that are timewise spaced in occurrence with respect to said first output pulses;
   a first control transistor connected with said first signal providing means;
   a first channel having first output means and first return means to be connected with a user;
   a second channel having second output means and second return means to be connected with a user;
   first and second capacitor means connected with said first and second output means, respectively;
   first and second diode means connected with said first and second return means, respectively;
   first constant current means including a first pair of transistors connected with said battery means, one of said transistors being a gate transistor responsive to said first control transistor the other of said pair being a regulating transistor cooperating with said gate transistor for providing a constant current at said first channel without use of inductive means, with said constant current being provided when said first control transistor is activated and otherwise isolating said first output means from said battery means;
   a second control transistor connected with said second signal providing means; and
   second constant current means including a second pair of transistors connected with said battery means, one of said transistors being a gate transistor responsive to said second control transistor the other of said pair being a regulating transistor cooperating with said gate transistor for providing a constant current at said second channel without use of inductive means, with said constant current being provided when said second control transistor is activated and otherwise isolating said second output means from said battery means;
   whereby only substantially rectangular pulses are provided to a user when connected with said first channel through said first capacitor means and said first output means with a return from said user being provided through said first return means and said first diode means, and whereby only substantially rectangular pulses are provided to said user when connected with said second channel through said second capacitor means and said second output means with a return from said user being provided through said second return means and said second diode means, said pulse output from said first channel being timewise spaced with respect to said pulse output from said second channel so that substantially complete isolation is established between said channels including isolation between said channels through said user when connected to receive said pulse outputs from said first and second channels.

2. The device of claim 1 wherein said first and second signal providing means of said oscillating means includes first and second integrating circuits with said first control transistor being connected to receive the output of said first integrated circuit and said second control transistor being connected to receive the output of said second integrated circuit.

3. The device of claim 1 wherein said device includes first and second buffer devices connected to receive the outputs from said first and second signal providing means, respectively, said first and second buffer means providing pulse outputs to said first and second control transistors, respectively.

4. The device of claim 1 wherein said device includes power indicating means having visual display means and means for causing said visual display means to be alternately energized and de-energized to indicate that the device is powered, said means for causing said visual display means to be alternately energized and de-energized including a low frequency oscillator having a charging capacitor and a programmable unit junction transistor.

* * * * *

UNITED STATES PATENT AND TRADEMARK OFFICE
CERTIFICATE OF CORRECTION

PATENT NO. : 4,632,117
DATED : December 30, 1986
INVENTOR(S) : Donald N. James et al It is certified that error appears in the above-identified patent and that said Letters Patent is hereby corrected as shown below:

On the title page inventors should read

-- Inventors: Donald N. James, Estes Park, Colo. and
Richard J. Shelquist, Longmont, Colo. --

Signed and Sealed this

Twenty-eighth Day of April, 1987

Attest:

DONALD J. QUIGG

*Attesting Officer*  *Commissioner of Patents and Trademarks*